(12) United States Patent
Keller

(10) Patent No.: US 6,966,773 B2
(45) Date of Patent: Nov. 22, 2005

(54) PERIODONTAL MEDICAMENT DELIVERY TRAY

(76) Inventor: Duane C. Keller, 3929 Bayless Ave., St. Louis, MO (US) 63125

(*) Notice: Subject to any disclaimer, the term of this patent is extended or adjusted under 35 U.S.C. 154(b) by 131 days.

(21) Appl. No.: 10/464,164

(22) Filed: Jun. 18, 2003

(65) Prior Publication Data
US 2003/0232311 A1 Dec. 18, 2003

Related U.S. Application Data

(63) Continuation-in-part of application No. 09/711,402, filed on Nov. 13, 2000, now abandoned.

(51) Int. Cl.[7] ............................................. A61C 17/02
(52) U.S. Cl. ....................................... 433/80; 433/215
(58) Field of Search ........................... 433/80, 89, 136, 433/215

(56) References Cited

U.S. PATENT DOCUMENTS

| | | | |
|---|---|---|---|
| 3,527,218 A | 9/1970 | Westine | |
| 3,874,084 A | 4/1975 | Cole | |
| RE28,667 E | 12/1975 | Gores | |
| 3,955,281 A | * 5/1976 | Weitzman | 433/25 |
| 4,064,628 A | 12/1977 | Weitzman | |
| 4,138,814 A | 2/1979 | Weitzman | |
| 4,173,219 A | 11/1979 | Lentine | |
| 4,428,373 A | 1/1984 | Seid et al. | |
| 4,531,914 A | 7/1985 | Spinello | |
| 4,560,351 A | 12/1985 | Osborne | |
| 4,902,227 A | 2/1990 | Smith | |
| 4,990,089 A | 2/1991 | Munro | |
| 5,076,791 A | 12/1991 | Madray, Jr. | |
| 5,085,585 A | 2/1992 | Zimble | |
| 5,098,303 A | 3/1992 | Fischer | |
| 5,129,824 A | 7/1992 | Keller | |
| 5,165,424 A | 11/1992 | Silverman | |
| 5,211,559 A | 5/1993 | Hart et al. | |
| 5,330,357 A | 7/1994 | Keller | |
| 5,443,386 A | 8/1995 | Viskup | |
| 5,575,654 A | 11/1996 | Fontenot | |

(Continued)

Primary Examiner—Ralph A. Lewis
(74) Attorney, Agent, or Firm—Polster, Lieder, Woodruff & Lucchesi, L.C.

(57) ABSTRACT

A tray fitted to at least some teeth of a patient's upper or lower arch is provided for the application of medications to the teeth and to adjacent gum tissue for treatment of periodontal disease. The tray is constructed from resilient material molded to conform to the teeth and gum tissue. The tray includes at least one recess formed to conform to the teeth. A seal surrounds the recess at a location corresponding to the patient's gum line for applying pressure at the patient's gum line when the patient's teeth are disposed in the recess. The recess contains a quantity of a medication. Upon installation of the tray on the patient's teeth, the medication is forced onto the surface of the teeth and subgingivally by the seal into any pockets in the patient's gums proximate the teeth. If desired, a propulsion agent can be disposed within the recess such that upon application of the tray onto the patient's teeth, the propulsion agent generates pressure within the recess so as to positively force the medication onto the patient's teeth and into any of the pockets in the patient's gums proximate the teeth. Methods for making the tray and for applying medication to a patient's teeth and gums also are disclosed.

14 Claims, 2 Drawing Sheets

U.S. PATENT DOCUMENTS

| | | |
|---|---|---|
| 5,725,843 A | 3/1998 | Fischer |
| 5,759,037 A | 6/1998 | Fischer |
| 5,770,182 A | 6/1998 | Fischer |
| 5,863,202 A | 1/1999 | Fontenot et al. |
| 5,895,218 A * | 4/1999 | Quinn et al. .................. 433/80 |
| 5,928,187 A | 7/1999 | Glukhov et al. |
| 6,030,213 A | 2/2000 | Trop |
| 6,247,930 B1 | 6/2001 | Chiang et al. |

* cited by examiner

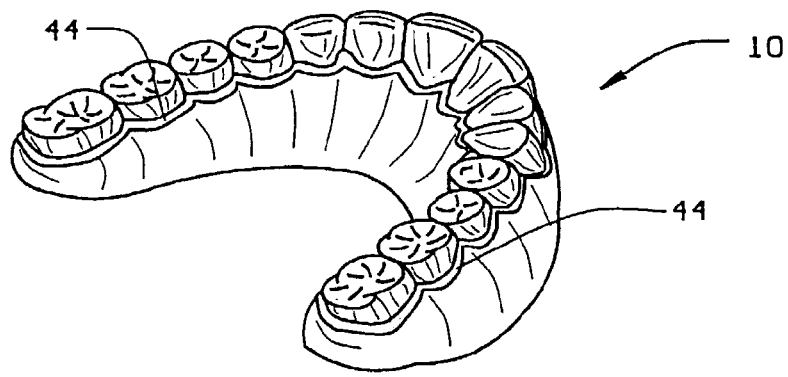
FIG. 1
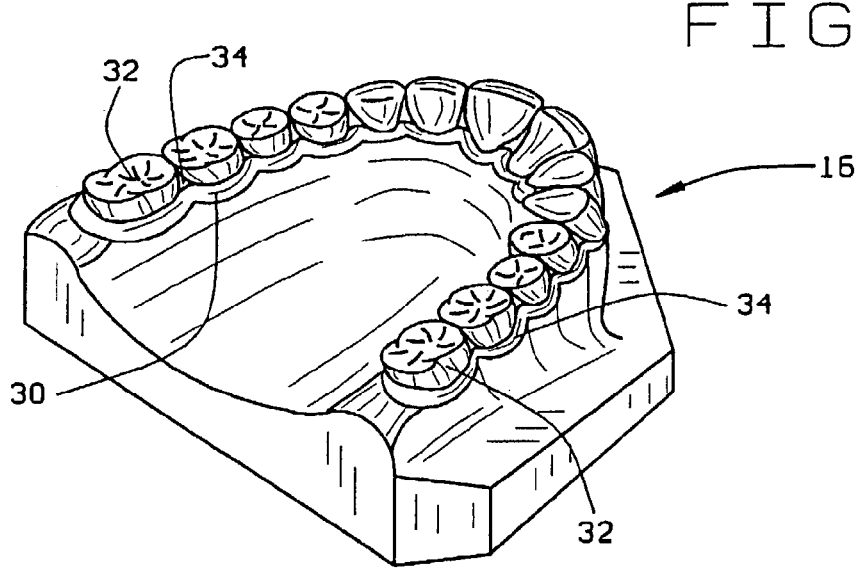
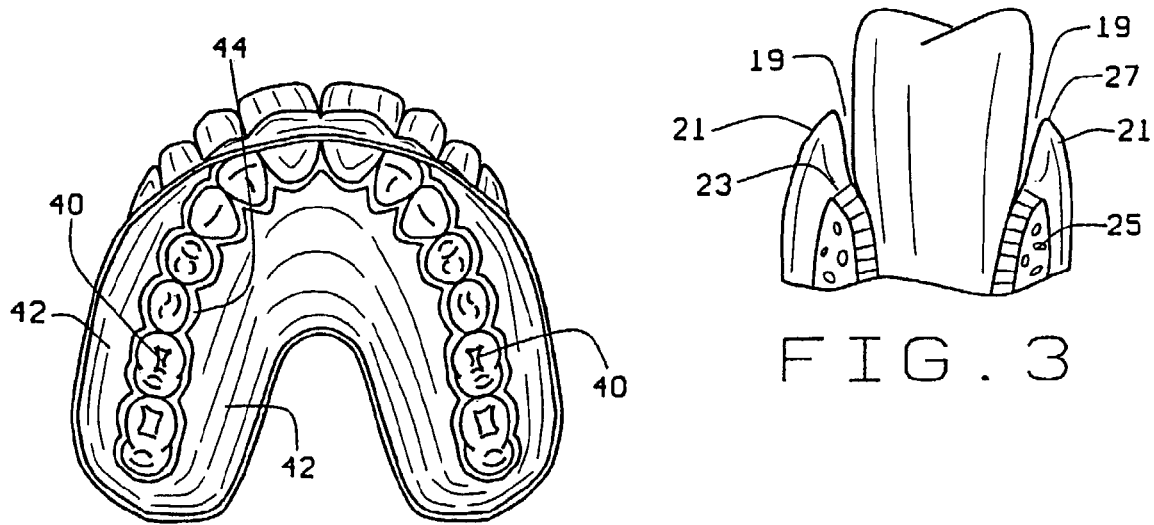
FIG. 3
FIG. 2

PERIODONTAL MEDICAMENT DELIVERY TRAY

CROSS-REFERENCE TO RELATED APPLICATIONS

The present application is a continuation-in-part of U.S patent application Ser. No. 09/711,402, filed Nov. 13, 2000, now abandoned the contents of which are expressly incorporated herein by reference.

STATEMENT REGARDING FEDERALLY SPONSORED RESEARCH OR DEVELOPMENT

Not Applicable.

BACKGROUND OF THE INVENTION

This invention relates to treatment of periodontal disease, and in particular to a dental tray and method for delivering medicament subgingivally to treat the infected area.

Periodontal (gum) disease affects a majority of adults at some time in their lives. Warning signs often are unnoticed until advanced stages of the disease. Treatment methods depend upon the type of disease and how far the condition has progressed. When deep pockets (3 mm or greater) exist between teeth and gums, it is difficult for the dentist to thoroughly remove plaque and tartar. While surgery may be necessary to reduce the depth of the pockets or to restore or reshape bone that has been destroyed, typically it is preferable to attempt to avoid such invasive procedures by treating the affected areas with antibacterial or antimicrobal agents (i.e., chemical, antibiotic, or other pharmacological agents) to restore periodontal health. Such antibacterial or antimicrobal agents have been found to control the growth of bacteria that create toxins and cause periodontal disease and encourage normal healing, thereby reducing the necessity or the invasiveness of periodontal or oral surgery.

Several methods have been developed for treating periodontal disease that enable medicament to be delivered to the infected site below the gingiva. For example, U.S. Pat. No. 5,085,585 to Zimble discloses an applicator of dental medicament and method of use. FIGS. 3, 4 and 5 of Zimble show the applicator of that invention being inserted over the teeth. Column 2, lines 14–21, explain that in Zimble a corner 24 of a shoulder or collar 22 reaches the gum pocket 32 and "causes the gum to be forced outwardly." In order to force the gum outwardly, the corner 24 of Zimble must enter the gum pocket to force the gum outwardly. Additionally, Zimble, at column 2, lines 24–27, reiterates that the collar enters the gum pocket. Zimble further discloses that the groove of approximately 2 mm by 2 mm is scribed into the periphery of the teeth of plaster model for forming the applicator 10. The groove is used to form the shoulder 22 (see col. 1, lines 63–65) which extends under the gum. It is therefore understood that the groove is formed within the tooth portion (not the gum portion) of the plaster mold so that the collar will be formed that will extend under the gum into the gum pocket.

Additionally, as set forth in U.S. Pat. No. 5,330,357, issued Jul. 19, 1994 to the present inventor, the disclosure of which hereby is incorporated by reference, medicament can be delivered in close proximity to the bone and supporting structure of the teeth by flossing using tufted floss, brushing using an interdental brush, injection using a syringe, or by hydrostatic or mastication pressure using a dental tray. Dental trays often are constructed from a soft plastic elastomeric material that is molded in place to a patient's teeth so as to firmly and closely fit in place on the patient's teeth, and a seal is made to hold the tray solidly against the dental tissues. Medicament is placed in recesses formed in the tray that are adapted to accommodate the patient's teeth, and then guided or forced along the teeth and into the gingiva by the sealing means to the infected site as the patient closes his jaw on the tray. A propulsion agent such as hydrogen peroxide also can be placed in the recesses to guide or force the medicament into the infected site as the hydrogen peroxide breaks down and increases the pressure within the recesses.

Other examples of dental trays are set forth in U.S. Pat. No. 4,902,227, issued Feb. 20, 1990 to Smith; U.S. Pat. No. 4,428,373 issued Jan. 31, 1984 to Seid et al.; and U.S. Pat. No. 4,138,814, issued Feb. 13, 1979 to Weitzman. While these types of dental trays do allow for application of the medicament subgingivally, none of these references discloses a dental tray that applies positive pressure to the tooth or edentulous region associated with the infected area to assist in forcing the medicament into the infected site.

U.S. Pat. No. 3,874,084, issued Apr. 1, 1975 to Cole, discloses a molded tooth cleansing and gingival therapeutic device that includes a plurality of bristles projecting inwardly from the inner walls of the upper and lower channels of a tray. The bristles are provided to clean food particles and bacteria from the surfaces of a user's teeth and the gingival crevices. The walls of the channels are of a sufficient thickness to form ridges or ledges extending away from the gingival lines. These ridges compress the gingiva to allow for cleansing of the gingival crevice between the teeth and gum and massaging of the free marginal gingival. However, the Cole device does not form a sufficient seal around the teeth and gums to allow for application of medicaments subgingivally and the penetration of the bristles would negate any positive pressure environment.

Thus, it is desirable to provide a dental tray and method for treatment of periodontal disease that provides a seal around teeth associated with the infected area to guide or force medication onto the surface of the teeth and subgingivally into the infected area. Such a seal can be modified to correspond to the nature of the diseased state, and also should assist in holding the medication in a desired location corresponding to the infected site. Such a tray and method of treatment also should be easily and conveniently administered by the patient, without special training or undue skill.

BRIEF SUMMARY OF THE INVENTION

Accordingly, one object of the present invention is to provide an improved periodontal medicament delivery tray and method for treating periodontal disease providing a seal around each tooth or edentulous region associated with the infected area to guide or force medication onto the surface of the teeth and subgingivally into the infected area.

Another object of this invention is to provide such a periodontal medicament delivery tray and method of treatment that reduces the invasiveness of and the need for periodontal surgery.

Still another object of this invention is to provide such a periodontal medicament delivery tray and method of treatment that can be conveniently and easily implemented by the patient, without requiring special training or undue skill.

Yet another object of this invention is to provide such a periodontal medicament delivery tray and method of treatment that impedes deterioration of the bone and gums, and promotes regeneration of supporting structures around the patient's teeth.

Another object of this invention is to provide such a periodontal medicament delivery tray that applies pressure from chewing or mastication to help to deliver or force the medicament to the source of the periodontal infection.

Another object of this invention is to provide such a periodontal medicament delivery tray that applies positive pressure around each tooth or edentulous region where periodontal disease is present to forcefully deliver medicament to the infected site below the gingiva.

Still another object of this invention is to provide such a periodontal medicament delivery tray that can be used as a protective mouthpiece during athletic activities.

Another object of this invention is to provide a dental tray that can be used as an anti-bruxing or anti-clenching appliance.

Yet another object of this invention is to provide a dental tray that can be used as a mouthpiece to properly relate the lower jaw to the upper jaw, and relax muscles and decrease pressure on the jaw joints.

Yet another object of this invention is to provide a dental tray that can be used as a delivery device for tooth whitening materials that would retain the whitening agents in the desired location because of the seal around the teeth.

These and other objects will become apparent to those skilled in the art in light of the following disclosure and accompanying drawings.

In accordance with the invention, generally stated, a tray fitted to at least some teeth of a patient's upper or lower arch is provided for the application of medications to the teeth and to adjacent gum tissue for treatment of periodontal disease. The tray is constructed from resilient material molded to conform to the teeth and gum tissue. The tray includes at least one recess formed to conform to the teeth. A seal surrounds the recess at a location corresponding to the patient's gum line for applying pressure at the patient's gum line when the patient's teeth are disposed in the recess. The seal and the length of the extension of the tray are modified to correspond to the disease state and are further modified to correspond to healing that occurs. The recess contains a quantity of a medication. Upon installation of the tray on the patient's teeth, the medication is forced onto the surface of the teeth and subgingivally by the seal into any pockets in the patient's gums proximate the teeth. If desired, a propulsion agent can be disposed within the recess such that upon application of the tray onto the patient's teeth, the propulsion agent generates pressure within the recess so as to positively force the medication onto the patient's teeth and into any of the pockets in the patient's gums proximate the teeth. The size of the seal and the extension of the tray beyond the seal enable the practitioner to manage the positive pressure environment to correspond to the diseased state of the patient and to modify this environment as healing occurs.

Another aspect of the present invention is of a dental tray for delivering medicament subgingivally including a molded body that conforms to at least a portion of a patient's dentition and adjacent gingival tissue. The body has at least one recess formed therein that is adapted to snugly accommodate the crown portion of at least certain of the patient's teeth. An extension of the elastomeric material projects outwardly from the body and surrounds the recess at locations corresponding to the patient's gum line. This extension supports the seal made around the gingiva. The recess contains a quantity of medicament, whereby medicament is forced subgingivally by the seal supported by the extension of elastomeric materials onto the patient's teeth when the patient's teeth are positioned in the recess. The thickness of the elastomeric material is also modified to correspond to the diseased state of the patient. Frail, fragile diseased tissues cannot withstand extreme forces and a light force must be supplied by the desired tray, seal and extension. As healing occurs, the thickness of the tray, the size of the seal and the length of the extension are modified to apply a more appropriate positive pressure to guide the medicaments to the desired locations. Likewise, the thickness of the tray is also modified to correspond to a patient's clenching or bruxing pattern as well as to position the mandible in a functional relationship to the mandible when a soft elastomeric appliance is indicated.

A third aspect of the present invention is that of a method for applying medication to at least certain of a patient's teeth and to gums proximate said teeth. This method includes the steps of: making a female impression of the patient's teeth and adjacent gums supporting the teeth from a suitable hardenable material; making a male model of the patient's teeth and surrounding gums from the female impression, the male model being formed of a suitable hardenable material; at the intersection of the gums and at least certain of the teeth of the male model, removing a bead (i.e., a desired amount or quantity dependent upon the status of the health of the tissue and the magnitude of the diseased state) of the hardenable material from the male model proximate the juncture of each of the teeth and the gum surrounding the teeth and/or between the teeth thereby to form at least one trough; forming a tray of moldable resilient elastomeric material molded over the male model having at least one recess representative of the teeth with a quantity of said resilient elastomeric material formed in the groove forming a seal of the desired size and an extension of the proper magnitude; applying a mediation into the recess of the tray; and fitting the tray with the medication in the recess onto the patient's teeth thereby to force the medication into contact with the patient's teeth and into pockets in the gum proximate the juncture with the teeth in accordance with the diseased status of the tissue.

Other objects and features will be apparent and in part pointed out hereinafter.

BRIEF DESCRIPTION OF THE SEVERAL VIEWS OF THE DRAWINGS

The objects of the invention are achieved as set forth in the illustrative embodiments shown in the drawings which form a part of the specification.

In the drawings,

FIG. 1 is a perspective new of the dental tray and mold of the present invention;

FIG. 2 is a bottom plan view of the dental tray;

FIG. 3 is a sectional view of a patient's tooth and adjacent soft tissue aid support structure;

Corresponding reference characters indicate corresponding parts throughout the several views of the drawings.

DETAILED DESCRIPTION OF THE INVENTION

Figure 4:
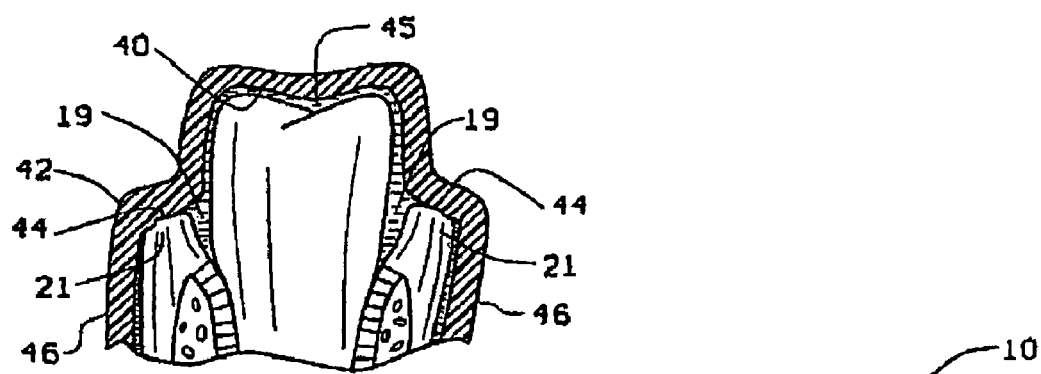
FIG. 4 is a sectional side view of the dental tray showing the patient's tooth and gingiva disposed therein.

The following detailed description illustrates the invention by way of example and not by way of limitation. This description will clearly enable one skilled in the art to make and use the invention, and describes several embodiments, adaptations, variations, alternatives and uses of the invention, including what I presently believe is the best mode of carrying out the invention.

Referring now to the drawings, and in particular to FIG. 1, a periodontal medicament delivery tray is shown, designated generally by reference numeral 10, for delivering medicament subgingivally to an infected area or areas. FIG. 3 shows a sectional view of a patient's tooth 18 and adjacent gingiva 21. Pockets or gingival crevices 19 exist between the patient's gingiva 21 and the teeth 18. Bacteria enter into the epithelial attachment, periodontal ligaments 23, and supporting jaw or cortical bone 25 through the gingival crevice 19. Pocket depths for gingival crevices 19 in a healthy mouth typically range from 0.05 to 3 mm. The tray 10 of the present invention is adapted for use on patients having periodontal disease with pocket depths greater than 3 mm, but may be used for patients having normal pocket depths in certain circumstances, such as clenching, bruxing, or application of medicaments to the teeth (tooth whitening agents, oral rinses, etc.).

To create the dental tray 10 of the present invention, a dentist takes an exact female impression (not shown) of the dentition, edentulous regions 26 (if any) and adjacent periodontal tissues 21 for a particular prospective user of the tray 10. To create the impression, the dentist can use any conventional impression-taking technique. For example, the patient can bite into a container filled with a suitable hardenable material such as, for example, an alginate material. When the alginate hardens, an accurate copy of the teeth 18 and adjacent periodontal tissue is produced. A suitable hardenable material such as, for example, plaster or dental stone is poured into the impression to create a male model or mold 16 that includes teeth 22 and gums 24 which are representative of the patient's teeth 18 and adjacent soft tissue 21. The mold 16 can be made for some or all of the upper and/or lower teeth, at locations corresponding to the infected sites into which the medicament will be delivered. The mold 16 also can be made for edentulous regions, if present, to allow a continuation of the positive pressure environment and for application of medicament to the tissues and/or bone (see FIG. 5).

After the mold has fully cured, the dentist or technician uses a hand-held tool (e.g., a round dental bar of desired dimension in a dental handpiece or laboratory engine) or a dental lathe device, or a computer directed removal device (such as a CAD-CAM) to remove the desired amount of the stone or plaster material at locations corresponding to desired level at the patient's gingival or gum line. The depth and magnitude of the removed materials is done in a specific manner to correspond to the diseased status of the patient's periodontal tissues. In other words, the dentist removes portions of the hardenable material from the mold 16 at the intersections of at least certain of the teeth 22 and gum 24 on the mold 16 to correspond to the diseased state of the patient. This creates one or more trough-like recesses or grooves of the desired depth and thickness (troughs 30) formed around the front and rear surfaces of affected teeth 22 above the gum line 28 of the mold 16 (FIG. 5) and this groove is extended interproximal between the teeth and continued around the border of any posterior tooth or edentulous area. In this manner, the groove 30 assists in forming a thickened lingual extension 46 of the tray 10 which is resiliently deflected by the gum when the tray 10 is installed within the patient's mouth. It is the resilient deflection of this lingual extension 46 that forms a seal 44 against the outer portion of a patient's gums. An extension of the resilient elastomeric material is also extended over the stone model to correspond to the patients gingival position. This extension is modified in length and the thickness of the materials is also modified to correspond to the diseases status of the patient to support the seal region and to further provide support to maintain the positive pressure environment. It should be noted that the lingual extension does not ever enter the gum pocket of the patient. In the model 16 shown in FIG. 1, the trough 30 is formed at the front and rear gum line for each tooth, and extends around the exposed surfaces of the upper second molars (or most posterior teeth of the patient) of the mold 16 and is made to extend between the teeth interproximally. One trough corresponding in depth and width to the status of the diseased state 30 is made around each tooth 22 or group of teeth 22 or edentulous region 26 (FIG. 5) where a seal 44 (discussed below) will be needed in the dental tray to force medicament subgingivally into the infected site or the bone. The troughs 30 preferably are formed around exposed surfaces of teeth 22 at the gum line 28, and extend into interproximal spaces 34 between adjacent teeth. Multiple troughs 30 can be formed at gum lines 28 of only certain teeth 22 or edentulous regions 26 corresponding to those that are affected by periodontal disease. Furthermore, the troughs 30 can be modified as needed and formed along only the front gum line or the rear gum line, if desired.

Figure 5:
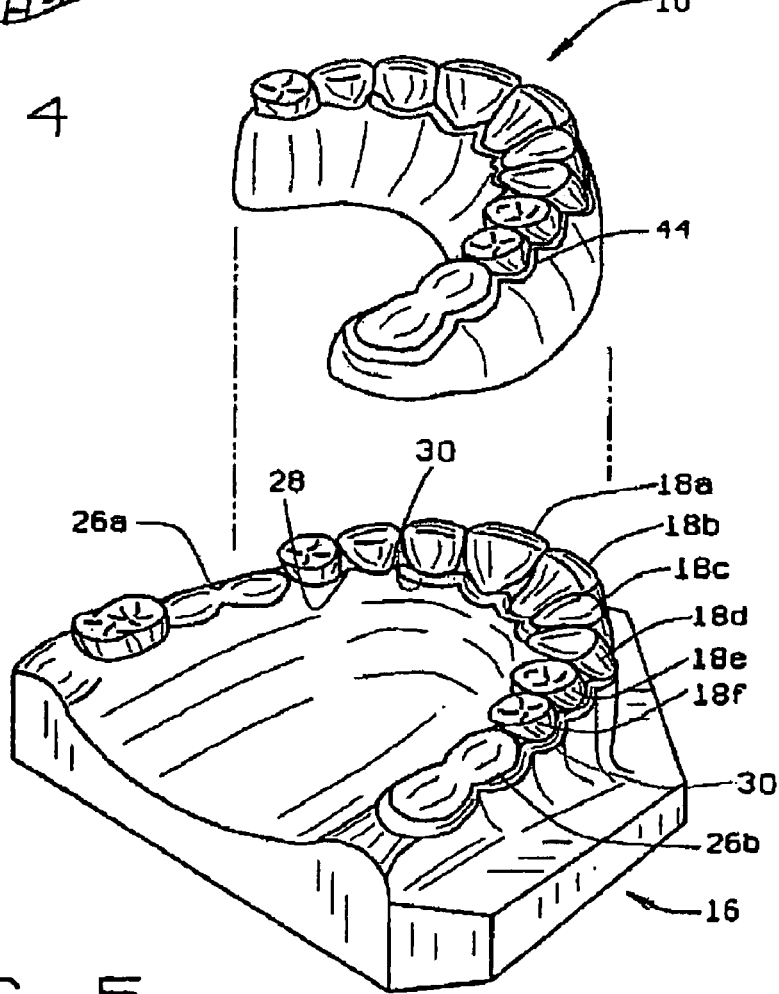
FIG. 5 is a perspective view of an alternative embodiment of the dental tray and mold.

FIG. 5 shows an alternative embodiment of the present invention that includes model or mold 16' and tray 10'. Mold 16' is for a patient's upper arch having two edentulous regions 26a, 26b (referred to collectively as edentulous regions 26) at locations corresponding to the upper right second bicuspid and first molar and the upper left first and second molars, respectively. Troughs 30 are formed at the gum line 28 for the central, left lateral, left cuspid, and left first and second bicuspid teeth 18a, 18b, 18c, 18d, 18e and 18f, respectively. Trough 30 also is formed around edentulous region 26b. A partial upper dental tray 10' also is shown, with a seal 44 (discussed below) formed in the tray 10 for teeth 18a–18f and region 26b. The elastomeric material is extended beyond the trough and over the edentulous area to support the trough and help provide a positive pressure environment in the desired regions. The extension of the tray and the thickness of the materials can be modified as needed to provide an environment that corresponds to the status of the diseased state.

The dental tray 10 is a precise form fitted flexible tray, preferably constructed from a moldable resilient material, such as a suitable soft plastic elastomeric material. One such elastomeric material that works well for this purpose is a mouthguard material that comes in varying thickness from 1 mm to 3 mm thick. The tray 10 is formed placing the appropriate thickness heated tray material on the model 16, and then applying positive air pressure to the tray material on the mold, or using a suction or other suitable methods to cure the tray material. The resulting dental tray 10 is molded as a replica of the original impression of the patient's teeth and periodontal tissue. As discussed below, the tray 10 also includes one or more seals 44 formed at locations corresponding to the troughs 30 that are added to the mold 16 by the dentist and an extension of the tray material to support the function of the seal in providing a positive pressure environment.

As shown in FIGS. 1 and 2, the dental tray 10 includes a molded body 42 having a substantially U-shaped configuration that conforms to the shape of the patient's dentition and adjacent soft tissue structures. The body 42 has form fitted recesses 40 therein that are adapted to snugly accommodate the crown portion of the patient's teeth 18. The tray 10 further includes a positive pressure seal of the desired depth and dimension of tray material formed in the trough of the model, with each positive pressure seal 44 that preferably surrounds at least a desired portion of one or more of the recessed areas 40. Thus, the seal 40 is formed at locations corresponding to the troughs 30 in the mold 16. As shown in FIG. 2, the seal 44 projects outwardly from body 42 of the tray 10 at locations corresponding to the juncture of the patient's teeth and gums (gum line). As discussed below, the seal 44 applies pressure at the patient's gum line when the patient's teeth 18 are disposed in the recess 40 to force medicament 45 disposed in the tray 10 subgingivally into any pockets in the patient's gums 21 proximate the teeth 18. The extension of the tray material beyond the seal further supports the seal in maintaining the desired environment that corresponds to the status of the diseased state of the patient. The tray 10 is shown in FIGS. 1 and 2 to be a full upper arch tray 10, but those skilled in the art will appreciate that a lower arch tray 10, dual arch tray 10 or partial arch tray 10 can be used, if desired.

Prior to applying a desired antimicrobal agent, osteogenic agent or other medicament or dental substance to the tray 10, the patient preferably inserts a small amount of a propulsion agent such as a gel-based antiseptic cleanser including hydrogen peroxide or other medicament preferably into the recess 40 of the tray 10. Then, an antimicrobal agent (e.g., a tetracycline solution) or similar desired medicament is placed in the tray 10 on top of the first medicament or propulsion agent. Alternatively, the antimicrobial agent can be included in a medicament that has a potential to provide pressure to force the medicament subgingival. Those skilled in the art will understand that a wide range of medicaments and propulsion agents can be used. For example, propulsion agents could include, but are not limited to, any one of the following peroxide compounds: peroxyl, gly-oxide, carbamide peroxide, peroxide containing materials, or any other agent that will undergo status altering processes providing a change in ambient or localized pressure gradients. These medicaments can also be modified to correspond to the diseased status of the patient's tissues. Such peroxide based propulsion agents are preferably, but not necessarily in a gel-like state to allow for ease of application to the tray and to the teeth and gum surfaces. Examples of antimicrobial agents that may be used with this invention include any one or more of the following anti-infective agents: penicillin, cephalosporings, carbapenem, monobactams, chloramphenicol, quinolones, floroquinolones, teteracyclines, macrolides, spectinomycin, vancomycin, lincosamides, aminoglycosides, colistimethates, ploymyxin, bactracin, vovobiocin, metronidazole, sulfnonnamides, nitrofurans, methenamines, and folate antagonists. In addition, well known antibiotic combinations may be used as well as antiviral, antiretroviral, immunologic agents, anti-infective agents, astringeents, topical ointments or liniments, osteogenic modifying materials or other antibiotics. The medicament and antimicrobal agent are collectively referred to medication 45, and schematically illustrated in FIG. 4.

The patient then fits the tray 10 onto the patient's appropriate arch, depending upon whether the tray 10 is designed for the patient's upper or lower arch or both. The hydraulic action of inserting the teeth 18 snugly into the tray 10 within the recess 40 tends to move the medicament 45 toward the gingiva 21 of the patient's mouth. As the hydrogen peroxide or other medicament breaks down and generates pressure within the recess 40, the seal 44 and the extension of the seal directs the medication 45 to the region of the infection and helps hold the medication in the desired location. When the patient chews or bites the tray 10, mastication forces forcibly squeezes the medicament 45 along the teeth 18 and into the gingiva 21 into the infected site or to the region of the bone. That is, as the seal 44 of the tray and the extension of the seal 10 applies pressure to the patient's gingiva 21 when the patient compresses his or her jaw on the tray 10, medicament 45 is forced onto the teeth 18 and gingiva 21 and into the gingival crevices. Gingival tissues 21 are compressed by the seal 44 and the extension of the elastomeric material beyond the seal as the patient closes his or her jaw against the tray 10 and the seal and extension of the seal guide the application of the medicament 45 subgingivally into the pockets (see FIG. 4). A portion of the pocket may be exposed when the gingiva 21 is compressed by the seal 44. Compression and release of the gingiva 21 by the seal 44 and extension of the seal because of mastication pressure also stimulates and massages the patient's gingiva 21.

Thus, the dental tray 10 allows for application of medicament 45 subgingivally by the patient several times each day. The patient can adjust the dosage or frequency of medicament delivery, as directed by the dentist or health care professional in accordance with the diseased status and also changes in the diseases status as healing occurs. While this method for treating periodontal disease is closely monitored by the dentist, use of the dental tray eliminates the need for the patient to make time consuming visits to the dentist for application of medicament to the infected site. Using the tray 10 to apply antibacterial or antimicrobal medicament to the site of infection subgingivally impedes deterioration of the bone and gum, and promotes healing and regeneration of the supporting bone structures around the patient's teeth. The tray can be modified or a new tray can be made to conform to the alterations in healing that occurs.

In practice, the severity of a patient's periodontal disease can be classified by any one of a variety of classification systems, such as the periodontal bleeding index; as class I, II, III or IV with class I being the least severe and class IV being the most severe. Class I periodontal bleeding index is determined when after 20 to 30 seconds of probing a single bleeding point is observed on the gums. Class II periodontal bleeding index is determined when after 20 to 30 seconds of probing a fine line of bleeding or several bleeding points are observed. Class III periodontal bleeding index is determined when after 20 to 30 seconds of probing the interdental triangle becomes more or less filled within blood. Class IV periodontal bleeding index is determined when after 20 to 30 seconds of profuse bleeding occurs. Likewise, other periodontal diagnostic systems can be used to document that diseased status and/or healing that occurs, the depth of the periodontal pocket and alterations in this depth, alterations in attachment levels and changes of the attachment level as well as various other diagnostic means.

Special care has to be taken when treating a person with class IV or an advanced state periodontal disease as the disease makes the gums very sensitive and the tissue very fragile. As a result, it is desirable to limit the amount of force applied to the gums of a class IV advanced disease patient by the propulsion agent and to maximize the force applied by the propulsion agent to the gums of a class I patient with less of a diseased status to maximize the application of medicament. The amount of force applied to the gums of a patient can be controlled in several ways. First, the amount of force can be reduced by minimizing the seal 44 at the gumline. As described above, the seal 44 is formed in the tray 10 by removing troughs 30 of material from the mold 16 at the gumline 28. Therefore, in order to treat a person with class IV or advanced periodontal disease, less material is removed from the troughs 30 to form a small seal. The result is less force applied to the gums of the patient by the seal and the propulsion agent. It has been found that it is desirable to remove about ¼ to ½ mm of material for patients with class IV or advanced periodontal disease, about ½ to ¾th_mm of material for patients with class III periodontal disease, about ¾ to 1 mm of material for patients with class II periodontal disease and about 1 to 1.5 mm of material for patients with class I periodontal disease.

Another method of minimizing or maximizing the pressure applied by the propulsion agent is to control the length of a lingual extension 46 of the tray 10. By shortening the lingual extension 46, propulsion agent more easily passes the seal 44 and amount of force applied to the gums is reduced. It has been found that for patients with class IV periodontal disease to have 0–1 mm of lingual extension, for patients with class III periodontal disease to have 1–2 mm of lingual extension, for patients with class II periodontal disease and about 2–3 mm of lingual extension and for patients with class I periodontal disease to have 3 mm or more of lingual extension.

Another method of minimizing or maximizing the pressure applied by the propulsion agent is to control the thickness of the tray 10. Because the tray resilient deflects as the seal 44 touches the bottom of the gumline 28, the ease of deflection is controlled by the type of material used and the thickness of the material. By making the material thinner for patients with class IV advanced periodontal disease, the propulsion agent can resiliently deflect the tray 10 and allow the propulsion agent to escape the tray without applying maximum force to the diseased areas and the patient's gums. It has been found that for patients with class IV periodontal disease the thickness is optimally 1–2 mm and increasing the thickness to 3 mm or more for patients with class I periodontal disease.

Finally, it is to be understood by one of ordinary skill in the art that the entire tray 10 does not have to be formed entirely for a particular class of periodontal disease, but can have portions that are formed to accommodate a more severe class of disease in one area and a less severe class of disease in another area. For example, a patient who suffers from class IV periodontal disease in a particular area of the gums or the patient's lower arch, but suffers from only class II periodontal disease in another region would be fitted with a tray that addressed this concern by applying less propulsive force to only the class IV region using one or more of the methods described above.

In view of the above, it will be seen that the several objects and advantages of the present invention have been achieved and other advantageous results have been obtained.

The foregoing description is set forth only for illustrative purposes only and is not meant to be limiting. As various changes could be made in the above constructions without departing from the scope of the invention, it is intended that all matter contained in the above description or shown in the accompanying drawings shall be interpreted as illustrative and not in a limiting sense. Numerous variations, within the scope of the appended claims will be apparent to those skilled in the art in light of the foregoing description and accompanying drawings. For example, the dental tray also can be used as a nighttime anti-bruxing or anti-clenching appliance. Furthermore, the tray can be used to properly relate the lower jaw to the upper jaw. The tray relaxes muscles and decreases pressure on the jaw joints. When two dental trays are used simultaneously for the upper and lower arches, the trays allow for control of jaw position, and can be used as an anti-snoring device. The trays also can be used as a protective mouthpiece for sporting activities.

What is claimed is:

1. A tray fitted to at least some teeth of a patient's upper or lower arch for the application of medications to the teeth and to adjacent gum tissue for treatment of periodontal disease,
    said tray being of resilient elastomeric material molded to substantially conform to said teeth and gum tissue,
    said tray having at least one recess formed to conform to the teeth,
    a raised seal surrounding said recess corresponding to a location along the patient's gum line for applying along only the outer portion of the patient's gum line when the patient's teeth are disposed in the recess,
    said recess containing a quantity of a medication and a propulsion agent such that upon installation of said tray on the patient's teeth the medication is forced onto the surface of the teeth and subgingivally by the seal into any pockets in the patient's gums proximate said teeth, and
    the propulsion agent generates pressure within said recess so as to direct the medication onto the patient's teeth and into any of said pockets in the patient's gums proximate said teeth.

2. The tray as set forth in claim 1 wherein said medication comprises an antimicrobial agent.

3. The tray as set forth in claim 1 wherein said propulsion agent is hydrogen peroxide.

4. The tray as set forth in claim 1 wherein said recess is defined by walls of said tray, said seal projecting outwardly from said walls such that the seal applies pressure to the patient's gums when the patient bites the tray.

5. The tray as set forth in claim 1 wherein said tray is constructed from a mold representative of the patient's teeth and surrounding gum tissue, said mold including at least one trough formed in the mold at a location corresponding to the patient's gum line, said seal being formed at a location corresponding to the trough of the mold.

6. The tray as set forth in claim 1 wherein said tray is altered to minimize or maximize the force applied to the patient's gums by the propulsion agent according to the stage of periodontal disease suffered by the patient.

7. The tray as set forth in claim 6 wherein the thickness of the seal is adjusted according to the stage of periodontal disease suffered by the patient such that the propulsion agent applies less force to a patient with more advance periodontal disease.

8. The tray as set forth in claim 6 wherein the thickness of the tray is adjusted according to the stage of periodontal disease suffered by the patient such that the propulsion agent applies less force to a patient with more advance periodontal disease.

9. The tray as set forth in claim 6 wherein the length of a buccal and lingual extension is adjusted according to the stage of periodontal disease suffered by the patient such that the propulsion agent applies less force to a patient with more advance periodontal disease.

10. A dental tray for delivering medicament subgingivally comprising a molded body that substantially conforms to at least a portion of a patient's dentition and adjacent gingival tissue, said body having at least one recess formed therein that is adapted to snugly accommodate the crown portion of at least certain of the patient's teeth, a raised seal projecting outwardly from said body and surrounding said recess at locations corresponding to only an outer portion of the patient's gum line proximate the patient's teeth, said recess containing a quantity of a medicament and a propulsion agent whereby said propulsion agent forces said medicament subgingivally by the seal and onto the patient's teeth.

11. A method of applying medication to at least certain of a patient's teeth and to gums proximate said teeth comprising the steps of:
   (a) making a female impression of the patient's teeth and adjacent gums supporting said teeth from a suitable hardenable material;
   (b) making a male model of the patient's teeth and surrounding gums from said female impression, said male model being formed of a suitable hardenable material;
   (c) at the intersection of the gums and at least certain of the teeth of said male model, removing an amount of said hardenable material from said male model proximate the juncture of each of said teeth and the gum surrounding said teeth thereby to form at least one trough;
   (d) forming a tray of moldable resilient material molded over said male model having at least one recess representative of said teeth with a bead of said resilient material formed in said groove forming a raised seal in a location such that the resilient material forming the seal will contact only an exterior surface of the patient's gum;
   (e) applying a medication and a propulsion agent into said recess of said tray; and
   (f) filling said tray with said medication and said propulsion agent in said recess onto the patient's teeth whereby the reaction of said propulsion agent forces said medication into contact with said teeth and into pockets in the gum proximate the juncture with said teeth.

12. The method as set forth in claim 11 wherein said medication is an antimicrobial agent.

13. The method as set forth in claim 11 wherein said step of applying a propulsion agent comprises applying a hydrogen peroxide compound into said recess.

14. The method as set forth in claim 11 wherein said step of applying a propulsion agent comprises applying a hydrogen peroxide gel into said recess.

* * * * *